United States Patent [19]

Hauck et al.

[11] 4,076,843
[45] Feb. 28, 1978

[54] 5,6,7,8-TETRAHYDRONAPHTHALENE HYPOTENSIVE AGENTS

[75] Inventors: Frederic Peter Hauck, Somerville; Christopher M. Cimarusti, Hamilton, both of N.J.; Joseph E. Sundeen, Yardley, Pa.

[73] Assignee: E. R. Squibb & Sons, Inc., Princeton, N.J.

[21] Appl. No.: 428,466

[22] Filed: Dec. 26, 1973

Related U.S. Application Data

[63] Continuation-in-part of Ser. No. 268,314 Jul. 3, 1972, abandoned.

[51] Int. Cl.² ........................................... A61K 31/135
[52] U.S. Cl. .................................................... 424/330
[58] Field of Search .......................... 260/574; 424/330

[56] References Cited

U.S. PATENT DOCUMENTS 3,579,582   5/1971   Symon ................................. 260/574

OTHER PUBLICATIONS

Chemical Abstracts, 63:8274-6 (1965).

Primary Examiner—Leonard Schenkman
Attorney, Agent, or Firm—Lawrence S. Levinson; Merle J. Smith; Donald J. Barrack

[57] ABSTRACT

5,6,7,8-Tetrahydronaphthalenes having the structure

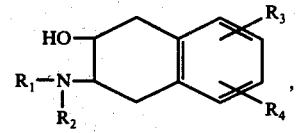

and the pharmaceutically acceptable salts thereof, are useful as blood pressure lowering agents. In the above formula $R_1$ can be hydrogen or alkyl; $R_2$ is alkyl; $R_3$ and $R_4$ can each be hydrogen, hydroxyl, alkoxy, or arylalkoxy, but both cannot be hydroxyl. Those compounds wherein at least one of $R_3$ and $R_4$ is other than hydrogen are novel, and constitute a part of this invention.

20 Claims, No Drawings

5,6,7,8-TETRAHYDRONAPHTHALENE HYPOTENSIVE AGENTS

This application is a continuation-in-part of U.S. Patent application, Serial No. 268,314, filed July 3, 1972, now abandoned.

BRIEF DESCRIPTION OF THE INVENTION 5,6,7,8-Tetrahydronaphthalenes having the structure

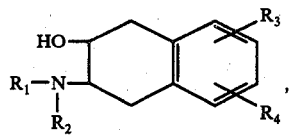

and the pharmaceutically acceptable salts thereof, have been found to be hypotensive agents. Compounds of formula I wherein at least one of $R_3$ and $R_4$ are other than hydrogen are novel, and as such constitute a part of this invention.

In formula I, and throughout the specification, the symbols are as defined below:

$R_1$ can be hydrogen or alkyl;
$R_2$ is alkyl; and
$R_3$ and $R_4$ can each be hydrogen, hydroxyl, alkoxy, or arylalkoxy, but at least one of $R_3$ and $R_4$ must be other than hydroxyl.

The term "alkyl" as used throughout the specification refers to both straight and branched chain alkyl groups having from one to eight carbon atoms, e.g., methyl, ethyl, propyl, isopropyl, t-butyl, heptyl, octyl, 2,2,4-trimethylpentyl, etc. Alkyl groups having one to four carbon atoms are preferred.

The term "alkoxy" as used throughout the specification refers to a group of the formula alkyl-O-, wherein alkyl is as defined above.

The term "arylalkoxy" as used throughout the specification refers to an alkoxy group (defined above) having the alkyl portion of the molecule substituted with an aryl group.

The term "aryl" as used throughout the specification refers to phenyl or phenyl substituted with one or two of the following substituents: halogen, alkyl, or alkoxy.

DETAILED DESCRIPTION OF THE INVENTION

The compounds of formula I can be prepared from naphthalene derivatives having the structure

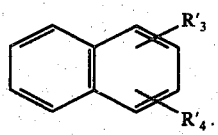

In formula II, and throughout the specification $R'_3$ and $R'_4$ can each be hydrogen or hydroxyl. A naphthalene of formula II can be reduced with a metal such as sodium or lithium in liquid ammonia containing an alkanol such as ethanol, isopropanol, t-butanol, etc. to obtain a 5,8-dihydronaphthalene having the structure

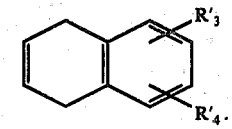

To prepare the 5,8-dihydronaphthalene starting materials necessary for the preparation of the compounds of formula I wherein $R_3$ or $R_4$ is alkoxy or arylalkoxy, the corresponding hydroxyl derivative of formula III is reacted with an alkyl halide or arylalkyl halide to yield a 5,8-dihydronaphthalene having the structure

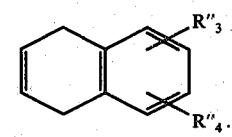

In formula IV, and throughout the specification, $R''_3$ and $R''_4$ can each be alkoxy or arylalkoxy. The reaction is carried out in a polar organic solvent, e.g., dimethylsulfoxide, dimethylformamide, etc., in the presence of an alkali metal alkoxide, e.g., sodium methoxide, potassium ethoxide, etc.

Reaction of a 5,8-dihydronaphthalene of formula III or formula IV with m-chloroperbenzoic acid yields a 5,6,7,8-tetrahydro-6,7-epoxynaphthalene having the structure

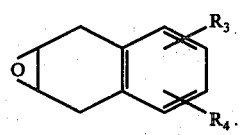

The reaction can be carried out by mixing m-chloroperbenzoic acid with a solution of a 5,8-dihydronaphthalene in an organic solvent, e.g., ethyl acetate. The resulting mixture is added to a mixture of ethyl ether and aqueous sodium bicarbonate, and mixed to form a 5,6,7,8-tetrahydro-6,7-epoxynaphthalene of formula V.

The compounds of formula I can be prepared by reacting a 5,6,7,8-tetrahydro-6,7-epoxynaphthalene of formula V with an amine having the formula

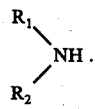

The reaction can be run in an organic solvent, e.g., ethanol, xylene, etc., at a temperature of from 50° C to 140° C, preferably from 110° C to 140° C. The reaction is run for about 5 hours to 24 hours, preferably 16 hours to 24 hours.

Other methods for the preparation of the compounds of formula I will be readily apparent to a person of ordinary skill in organic chemistry. The preparation of compounds of formula I containing an alkoxy group in the aromatic ring can be accomplished by first preparing the corresponding phenolic derivative. Reaction of the phenolic compound with a diazoalkane in an organic solvent yields the desired alkoxy derivative.

Both the cis and trans isomers of the compounds of formula I are specifically contemplated for use in this invention. The cis compounds can be prepared from the corresponding trans compounds using an inversion technique. In this procedure a trans vicinal primary amino alcohol is reacted with benzoyl chloride in benzene in the presence of a base to yield the corresponding benzamidoalcohol. The benzamidoalcohol is then converted to the corresponding cyclic oxazolidine with thionyl chloride, which is hydrolyzed in dilute acid to the cis vicinal primary amino alcohol and alkylated by well known methods, e.g., condensation with a ketone followed by catalytic reduction.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

The 5,6,7,8-tetrahydronaphthalenes of formula I, and the pharmaceutically acceptable acid addition salts thereof, are useful as hypotensive agents in mammals, e.g., domestic animals such as dogs, cats, etc. Daily doses of from 5 to 50 mg/kg, preferably about 5 to 25 mg/kg can be administered in single or divided doses.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples further illustrate the preparation of the compounds of this invention.

EXAMPLE 1

6,7-trans-5,6,7,8-Tetrahydro-7(and 6)-(isopropylamino)-1,6(and 7)-naphthalenediol, hydrochloride A. 6,7-Epoxy-5,6,7,8-tetrahydro-1-naphthol acetate A solution of 101 g of 5,8-dihydro-1-naphthol acetate in 1.5 liters of methylene chloride is cooled to 0° C and 89 g of m-chloroperbenzoic acid is added over a period of 5 minutes and the mixture is stirred overnight at room temperature.

The suspension is poured into a mixture of 500 ml of 10% sodium hydroxide and 1000 g of ice. The aqueous layer is extracted with methylene chloride (two 500 ml portions), and the combined organic layers are washed with water and saturated sodium chloride solution, dried and evaporated in vacuo to give 105 g of pink solid.

B. 6,7-trans-5,6,7,8-Tetrahydro-7(and 6)-(isopropylamino)-1,6(and 7)-naphthalenediol, hydrochloride A mixture of 6,7-epoxy-5,6,7,8-tetrahydro-1-naphthol acetate (10.2 g) and isopropylamine is charged to a small bomb and heated overnight in an oil bath maintained at 100° C. After cooling, the excess amine is removed in vacuo leaving a dark brown viscous material which is chromatographed, on activity 3 neutral alumina. Fractions eluted with 10–20% methanol in chloroform yield crystalline material on standing under hexane. Two recrystallizations from ether give a sample melting at 112°–117° C. This is dissolved in isopropyl alcohol-ether and converted to the hydrochloride by adding a solution of hydrochloric acid in isopropyl alcohol. The white hydrochloride is recrystallized from isopropyl alcohol-methanol-ether to give 2.2 g of the title product, melting point 207°–210° C.

EXAMPLE 2 trans-7(and 6)-(Dimethylamino)-5,6,7,8-tetrahydro-1,6(and 7)-naphthalenediol

A mixture of 10.2 g of 6,7-epoxy-5,6,7,8-tetrahydro-1-naphthol acetate (prepared as described in Example 1) and 50 ml of anhydrous dimethylamine is heated overnight in a small Paar bomb (oil bath temperature = 100° C ± 5° C, internal pressure = 140 psi). After cooling the reaction mixture, excess dimethylamine and N,N-dimethylacetamide are removed in vacuo, yielding 11.65 g of dark viscous oil. This material is dissolved in benzene and applied to a column of basic alumina (Activity III, 350 g). Elution with benzene and benzene/chloroform mixtures give small amounts of non-polar material. Elution with chloroform yields 4.36 g of crude trans-7-(dimethylamino)-5,6,7,8-tetrahydro-1,6-naphthalenediol, melting point 179°–183° C after trituration with ether. Elution with 5% methanol/chloroform gives 3.12 g of trans-6-(dimethylamino)-5,6,7,8-tetrahydro-1,7-naphthalenediol, melting point 168°–170° C after trituration with ether.

Two recrystallizations from ethyl acetate/benzene of trans-7-(dimethylamino)-5,6,7,8-tetrahydro-1,6-naphthalenediol give 1.93 g of colorless crystals melting point 181.5°-183.5° C.

Two recrystallizations from ethyl acetate/benzene of trans-7-(dimethylamino)-5,6,7,8-tetrahydro-1,6-naphthalenediol give 1.22 g of colorless crystals, melting point 169.5°-171° C.

Anal. Calc'd for $C_{12}H_{17}NO_2$: C, 69.54; H, 8.27; N, 6.75.

Found: C, 69.69; H, 8.47; N, 6.76.

EXAMPLE 3 trans-1,2,3,4-Tetrahydro-3-[(1-methylethyl)amino]-5,8-dimethoxy-2-naphthalenol

A. 4a,5,8,8a-Tetrahydro-1,4-naphthaquinone

The 1,3-butadiene adduct of p-quinone is prepared as described by van Tamelen, et al, JACS, 91, 7315 (1969). An amount of 500 ml of liquified 1,3-butadiene is added to a mixture of 500 g of p-quinone in 3.5 liters of benzene at 0° C. The 5-liter round bottom flask is sealed with a tightly wired rubber stopper and stored in the dark at room temperature for 23 days. The mixture is treated with charcoal, filtered, and evaporated in vacuo. Recrystallization from petroleum ether (12 liters) gives 456.5 g of 4a,5,8,8a-tetrahydro-1,4-naphthaquinone, melting point 52°-57° C.

B. 5,8-Dihydro-1,4naphthalenediol

As described in Ber., 62, 2345 (1929) an amount of 1 ml of a saturated solution of hydrogen bromide gas in glacial acetic acid is added to a mixture of 104 g of 4a,5,8,8a-tetrahydro-1,4-naphthaquinone in 174 ml of glacial acetic acid. The solution is stirred for 5 minutes at room temperature before a vigorous exothermic reaction takes place (temperature 25°-110° C over a 2 minute period) giving a light tan solid. The solid is collected and washed with hexane to give 100.5 g of 5,8-dihydro-1,4naphthalenediol, melting point 208°-211° C.

C. 5,8-Dihydro-1,4-dimethoxynaphthalene

A suspension of 63.18 g (0.39 mole) of 5,8-dihydro-1,4-naphthalenediol in 300 ml of absolute ethanol is heated briefly until solution is achieved. To this hot stirred solution is added alternately in five portions a solution of 40 g of sodium hydroxide in 100 ml of water, and 120 g of dimethyl sulfate. The heat evolved during the addition causes the solution to reflux. After the addition is complete a solution of 10 g of sodium hydroxide in 20 ml of water is added and the mixture is heated overnight at 75° C.

The ethanol is removed in vacuo, and the aqueous residue is thoroughly extracted with ether. The combined ether extracts are washed with saturated aqueous sodium chloride, dried, and concentrated in vacuo to give 70.40 g of tan crystals of 5,8-dihydro-1,4-dimethoxynaphthalene, melting point 48°-50° C.

D. 6,7-Epoxy-5,6,7,8tetrahydro-1,4-dimethoxynaphthalene

To a well-stirred solution of 70.40 g of 5,8-dihydro-1,4-dimethoxynaphthalene in 1.5 liters of methylene chloride at 0°-5° C is added 81.5 g of 85% m-chloroperbenzoic acid over 5 minutes, and the resulting mixture is stirred overnight at room temperature. The mixture is poured into excess 10% aqueous sodium hydroxide (0°-5° C) and the layers are separated. The aqueous layer is washed with methylene chloride and the combined organic layers are washed with 10% aqueous sodium hydroxide, saturated aqueous sodium chloride, dried, and concentrated in vacuo to give a tan solid. Trituration with isopropyl ether gives 45 g of tan crystals, melting point 127°-130° C. Recrystallization from isopropyl ether gives needles of 6,7-epoxy-5,6,7,8-tetrahydro-1,4-dimethoxynaphthalene, melting point 130°-131.5° C.

E. trans-1,2,3,4-Tetrahydro-3-[(1-methylethyl)amino]5,8-dimethoxy-2-naphthalenol A mixture of 10.3 g of 6,7-epoxy-5,6,7,8-tetrahydro-1,4-dimethoxynaphthalene in 50 ml of isopropylamine containing 2.93 ml of absolute ethanol is heated overnight in a small Parr bomb at 105° C ± 5° C (internal pressure = 75-100 psi). The cooled reaction mixture is concentrated in vacuo to 11.51 g of tan solid. Trituration with ether gives 10.1 g of material, melting point 141-144° C. Two recrystallizations from ethyl acetate give 7.0 g of trans-1,2,3,4-tetrahydro-3-[(1-methylethyl)amino]-5,8-dimethoxy-2-dimethoxy-2-naphthalenol, melting point 144°-145° C.

Anal. Calc'd for $C_{15}H_{23}O_3N$: C, 67.89; H, 8.74; N, 5.23.

Found: C, 67.65; H, 8.98; N, 5.14.

EXAMPLE 4 trans-5,6,7,8-Tetrahydro-7(and 6)-[(1-methylethyl)-amino[-1,6(and 7)-naphthalenediol A mixture of 15.3 g of 6,7-epoxy-5,6,7,8-tetrahydro-1-naphthol acetate (prepared as described in Example 1), 4.4 ml of absolute ethanol, and 75 ml of isopropylamine is heated overnight in a small Parr bomb at 125° C ± 5° C (internal pressure = 75-100 psi). The cooled reaction mixture is concentrated in vacuo to a viscous oil. This is dissolved in ether and thoroughly extracted with 5% hydrochloric acid. The pH of the combined acid extracts is adjusted to 7-8 with aqueous sodium hydroxide, and this is thoroughly extracted with ethyl acetate. The combined extracts are dried and concentrated in vacuo to give 16.66 g of viscous oil (contains N-isopropylacetamide). Trituration of this oil with chloroform yields 10.9 g of crude trans-5,6,7,8-tetrahydro-6-[(1-methylethyl)amino]-1,7-naphthalenediol, melting point 132°-136° C. Two recrystallizations of trans-5,6,7,8-tetrahydro-7-[(1-methylethyl)amino]-1,6-naphthalenediol from ethyl acetate yields the analytical sample (5.25 g) melting point 152°-154° C.

Two recrystallizations of crude trans-5,6,7,8-tetrahydro-6-[(1-methylethylamino)amino]-1,7-naphthalenediol (2.57 g) from ethyl acetate yields the analytical sample (1.07 g), melting point 138°-140° C.

EXAMPLE 5 trans-7(and 6)-[(1,1-Dimethylethyl)amino]-5,6,7,8-tetrahydro-1,6(and 7)-naphthalenediol A mixture of 15.3 g of 6,7-epoxy-5,6,7,8-tetrahydro1-naphthol acetate (prepared as described in Example 1), 4.4 ml of absolute ethanol, and 75 ml of t-butylamine is heated at 130° C ± 5° C in a small Parr bomb for 24 hours. The cooled reaction mixture is concentrated in vacuo to a dark viscous oil, which is taken up in ether and thoroughly extracted with 5% hydrochloric acid. The pH of the combined extracts is adjusted to 7.0-7.5 with aqueous sodium hydroxide, and this is thoroughly extracted with ethyl acetate. The combined extracts are dried and concentrated in vacuo to yield 12.81 g of viscous oil (contains N-t-butylacetamide). The crude oil is dissolved in benzene and applied to a column of basic alumina (400 g, Activity III). Elution with benzene and benzene/chloroform mixtures gives non-polar material, including crystalline N-t-butyl acetamide. Elution with chloroform yields 3.87 g of crude trans-7-[(1,1-dimethylethyl)amino]-5,6,7,8-tetrahydro-1,6-naphthalenediol, melting point 123°–127° C, after trituration with ether. Elution with 5% methanol/chloroform yields 2.56 g of crude trans-6-[(1,1-dimethylethyl)amino]-5,6,7,8-tetrahydro-1,7-naphthalenediol, melting point 97°–102° C, after trituration with ether.

Two recrystallizations of crude trans-7-[(1,1-dimethylethyl)amino]-5,6,7,8-tetrahydro-1,6naphthalenediol from ethyl acetate gives the analytical sample, melting point 126.5°–128° C.

Anal. Calc'd for $C_{14}H_{21}NO_2$: C, 71.45; H, 9.00; N, 5.95

Found: C, 71.67; H, 9.21; N, 5.90.

Two recrystallizations of crude trans-6-[(1,1-dimethylethyl)amino]-5,6,7,8-tetrahydro-1,7-naphthalenediol from benzene gives the analytical sample, melting point 152°–154° C.

Anal. Calc'd for $C_{14}H_{21}NO_2$: C, 71.45; H, 9.00; N, 5.95.

Found: C, 71.71; H, 9.25; N, 5.77.

EXAMPLE 6 trans-1,2,3,4-Tetrahydro-5-methoxy-3-[(1-methylethyl)amino]-2naphthalenol

A solution of 25 mmoles of diazomethane (prepared from 6.0 g of N-methyl-N'-nitro-N-nitrosoguanidine) in ether at 0°–5° C is added to a solution of 4.42 g of trans-5,6,7,8-tetrahydro-7-[(1methylethyl)amino]-1,6-naphthalenediol (see Example 4) in 25 ml of methanol, and the resulting solution is left at 0°–5° C for 48 hours. The excess diazomethane is decomposed by the addition of a few drops of dilute aqueous acetic acid, and the resulting solution is concentrated in vacuo. The residue is partitioned between 5% aqueous sodium hydroxide and ethyl acetate, and the layers are separated. The ethyl acetate solution is washed with 5% aqueous sodium hydroxide, saturated aqueous sodium chloride, dried, and concentrated in vacuo to give a solid. Trituration of this with isopropyl ether gives 3.14 g of crude product, melting point 107°–110° C. Two recrystallizations from ethyl acetate give the analyical sample (1.9 g), melting point 110°–112° C.

Anal. Calc'd for $C_{14}H_{21}NO_2$: C, 71.45; H, 9.00; N, 5.95. Found: C, 71.35; H, 9.30; N, 5.99.

EXAMPLE 7 trans-1,2,3,4-Tetrahydro-3[(1-methylethyl)amino]-2,6(or 7)-naphthalenediol

A. 1,2,3,4-Tetrahydro-2,3-epoxy-6-naphthol acetate

A solution of 15.12 g of 1,4-dihydro-6-naphthol acetate in 160 ml of dichloromethane is cooled to 0° C while 10.5 g of m-chlorobenzoic acid is added over 10 minutes. The mixture is stirred overnight at room temperature and then poured into a slurry of 100 g of ice and 50 ml of 10% aqueous sodium hydroxide. The layers are separated, the aqueous layer re-extracted with dichloromethane (two 100 ml portions), and the combined extracts are washed with water, dried, and evaporated in vacuo to give 16 g of the title compound as a yellow liquid.

B.
trans-1,2,3,4-Tetrahydro-3-[(1-methylethyl)amino]-2,6(or 7)-naphthalenediol

A mixture of 15.3 g of 1,2,3,4-tetrahydro-2,3-epoxy-6-naphthol acetate, 4.4 ml of absolute ethanol and 75 ml of isopropylamine is heated overnight in a small Paar bomb at 130° C ± 10° C. The cooled reaction mixture is concentrated in vacuo. Trituration of this material with ether gives 11.25 g of a mixture of isomers having a melting point of 116°–150° C. The mother liquor from trituration yields an additional 0.9 g of this mixture. The mother liquor from the second trituration is concentrated in vacuo and applied to a column of basic alumina (Activity III). Elution with 5% methylene/chloroform gives 1.47 g of crude isomer B, melting point 125°–130° C after trituration with ether.

Three recrystallizations of the above 11.25 g mixture from ethyl acetate gives pure isomer A, melting point 153.5°-155° C.

Two recrystallizations of the 1.47 g sample of crude isomer B from ethyl acetate gives pure product, melting point 134.5°–135.5° C.

EXAMPLE 8 cis-1,2,3,4-Tetrahydro-3-[(1-methylethyl)amino]-2-naphthalenol, hydrochloride (1:1)

A. trans-3-Amino-1,2,3,4-tetrahydro-2-naphthalenol, hydrochloride (1:1)

A solution of 9.29 g of sodium azide in 20 ml of water is added dropwise to a solution (40° C) of 5,6,7,8-tetrahydro-6,7-epoxy-1-naphthol (prepared as described in Example 11) in 200 ml of dioxane, and the resulting solution is refluxed overnight. The cooled reaction mixture is filtered and concentrated in vacuo, and the residue is taken up in chloroform, washed with water, saturated salt solution, dried, and concentrated in vacuo to 18.21 g of purple liquid.

The crude azide is dissolved in 250 ml of absolute ethanol and hydrogenated in the presence of 1.0 g of prereduced platinum oxide (Parr shaker-24 hours). During the course of the hydrogenation, the Parr bottle is vented and refilled ten times. The catalyst is filtered off, and the filtrate is concentrated in vacuo to a dark oil which partially crystallizes on standing. The crude amino-alcohol is dissolved in isopropanol/methanol and treated with hydrogen chloride saturated isopropanol, to afford 7.0 g of crystalline hydrochloride. Two recrystallizations of 1.5 g of this material from isopropanol/methanol gives the analytical sample of the title compound, melting point 264°–266° C, dec.

B.
trans-3-Benzamido-1,2,3,4-tetrahydro-2-naphthalenol

To a well stirred solution of 3.62 g of trans-3-amino-1,2,3,4-tetrahydro-2-naphthalenol, hydrochloride (1:1) in 30 ml of water at 0–5° C is added 2.1 ml of benzoyl chloride in 10 ml of benzene. To this stirred two-phase mixture is added, over 30 minutes at 0°–5° C, a solution of 1.45 g of sodium hydroxide in 30 ml of water—precipitation of a pink solid begins immediately. After stirring the mixture for an additional 2 hours at 0°–5° C, the solid is filtered, washed with ether, and dried in vacuo to give 4.2 g of crude trans-3-benzamido-1,2,3,4-tetrahydro-2-naphthalenol.

C. cis-3-Amino-1,2,3,4-tetrahydro-2-naphthalenol, hydrochloride (1:1)

To 10 ml of thionyl chloride is added, in portions over a 30 minute period, 3.48 g of trans-3-benzamido-1,2,3,4-tetrahydro-2-naphthalenol. The mixture is then heated at 50° C for 2.5 hours. The thionyl chloride is removed in vacuo, the residue taken up in 40 ml of 10% hydrochloric acid, and the solution is refluxed overnight. The reaction mixture is cooled, the precipitated benzoic acid is filtered off, and the filtrate is concentrated in vacuo to give 2.6 g of crystalline hydrochloride. Recrystallization from isopropanol/methanol gives the analytical sample of the title compound, melting point 269°–271° C.

Anal. Calc'd for $C_{10}H_{13}ON \cdot HCl$: C, 60.16; H, 7.07; N, 7.01; Cl, 17.76. Found: C, 60.28; H, 6.87; N, 6.99; Cl, 17.67.

D. cis-1,2,3,4-Tetrahydro-3-[(1-methylethyl)amino]-2-naphthalenol, hydrochloride (1:1)

A solution of 1.08 g of amino-alcohol (from the above hydrochloride) and 2.2 ml of acetone in 100 ml of absolute ethanol is hydrogenated in the presence of 1.0 g of pre-reduced platinum oxide. After uptake of one equivalent of hydrogen, the catalyst is filtered off, and the filtrate is concentrated in vacuo. The solid residue is taken up in isopropanol/ether, chilled, and treated with excess hydrogen chloride saturated isopropanol to afford 1.00 g of crude product. Two recrystallizations from isopropanol/methanol give the analytical sample of cis-1,2,3,4-tetrahydro-3-[(1-methylethyl)amino]-2-naphthalenol, hydrochloride (1:1), melting point 232°–234° C, dec.

Anal. Calc'd for $C_{13}H_{19}NO \cdot HCl$: C, 64.57; H, 8.34; N, 5.79; Cl, 14.68. Found: C, 64.54; H, 8.16; N, 5.76; Cl, 14.91.

EXAMPLE 9 trans-1,2,3,4-Tetrahydro-3-[(1-methylethyl)amino]-2-naphthalenol

A. 6,7-Epoxy-5,6,7,8-tetrahydronaphthalene

A solution of 1,4-dihydronpahthalene (32.5 g) in 300 ml of chloroform is cooled in an ice bath and, while stirring, is treated portionwise with 61 g of 85% m-chloroperbenzoic acid. The mixture is stirred overnight at room temperature. After cooling in an ice bath, the solids are removed by filtration. The filtrate is washed twice with 5% potassium carbonate solution, dried over magnesium sulfate, filtered and the solvent is removed in vacuo leaving 37.7 g of yellow partially crystalline material. This is distilled from a small amount of solid potassium carbonate. After some low boiling material is removed, 16.0 g of 6,7-epoxy-5,6,7,8-tetrahydronaphthalene is collected, boiling point 95°–110° C at 0.1 mm.

B. trans-1,2,3,4-Tetrahydro-3-[(1-methylethyl)amino]-2-naphthalenol

A solution of 8 g of 6,7-epoxy-5,6,7,8-tetrahydronaphthalene in 50 ml each of isopropylamine and ethanol is heated in a Parr bomb at 130° C for two days. The solution is cooled and evaporated in vacuo. The residue is triturated with hexane to give 4.8 g of an off-white solid. 2.4 g of the solid is dissolved in ethyl acetate methanol (75:25) and crystallized to give 0.40 of white solid. The filtrate is then concentrated on the steam bath to about 15 ml, and diluted with an equal volume of hexane. It crystallizes to give 1.37 g of trans-1,2,3,4-tetrahydro-3-[(1-methylethyl)amino]-2-naphthalenol, melting point, 73°–76° C.

Anal. Calc'd for $C_{13}H_{19}NO$: C, 76.05; H, 9.33; N, 6.82. Found: C, 75.85; H, 9.55; N, 6.73.

The hypotensive activity of the compounds of formula I is tested using the following method.

Male, spontaneously hypertensive Wistar rats (250 to 300 gms) are prepared surgically according to the method of Weeks and Jones *Biol. Med.* 104: 646 (1960). Coiled PE 10 tubing is joined by heating to a length of PE 20 tubing. After making an abdominal incision in an anesthetized rat, the PE 10 tubing is inserted, via a needle puncture, a short distance into the abdominal aorta terminating below the origin of the renal arteries. The PE 20 portion of the cannula is passed subcutaneously to exit at the back of the neck. The cannula is filled with saline and plugged with a 21 g needle stylet wire.

After a minimum of two days, the rat is placed in a harness similar to Model 1602, Lehigh Valley Electronics. The harness is secured to one end of a tightly-wound steel spring. The other end of the spring is passed through the top of the cage containing the rat and is attached to the lower end of a feed-through swivel (Sage, Model 120). The steel spring serves as a protective cover for the PE 100 tubing within it that connects the rat's arterial cannula to the swivel connector. The upper portion of the swivel is provided with two connections, one to a Statham transducer through a rotary fluid switch (Scanivalve, Inc.), the other to a pressurized saline reservoir that provides a slow flow of saline into the arterial cannula to minimize the packing of cells at its tip.

The blood pressures of 10 rats can be measured at one time using the rotary fluid switch and a single transducer. The switch is programmed to advance through 12 steps, each of 12 seconds duration. Within each cycle the following pressures are recorded: (1) atmospheric pressure, (2) 200 mm Hg static pressure, (3) rate #1, etc. to (12) rat #10. At the end of each cycle the switch returns to position #1, the cycles are repeated at 5 minute intervals throughout the experimental period.

The signal from the transducer is recorded on magnetic tape (Hewlett-Packard, Model 3960A Portable Instrumentation Recorder) for subsequent analysis.

A d.c. voltage signal is introduced through a manually operated toggle switch to a second track on the magnetic tape to indicate the time when the rats are given a drug. Drug dosage is carried out at the end of a 30-minute control period and during the approximately 2½ minute interval between completion of one cycle of the rotary fluid switch and commencement of the subsequent cycle. In this way artifacts resulting from handling the animals during drug administration are not introduced onto the tape recording. A timing signal from a crystal oscillator is recorded on a third track of the tape to permit compensation by the computer for variations in tape speed during playback of the data into the recorder.

Following the experiment, the recorded data is introduced into a PDP-11 digital computer through an A/D converter. At this time the following data are fed into the computer: date of experiment, rat number and sex, drug code number, dose and route of administration, pH of the solution used and the computer run number. The computer is programmed to sense and store the peak, nadir and integral of each pulse, as well as the number of pulses during 10 seconds of each scan on each rat. These parameters are averaged and stored as the systolic, diastolic and mean blood pressure and the heart rate for that time.

Changes in mean blood pressure are rated as follows:

|  | Rating |
|---|---|
| 0 to 10% - equivocal | 0 |
| 11 to 20% - slight | 1 |
| 21 to 30% - moderate | 2 |
| >30% - marked | 3 |

The following table shows the changes in mean blood pressure (all changes were *decreases*) for spontaneously hypertensive rats treated with the compound indicated. The change in mean blood pressure is rated using the 0–3 scale described above.

TABLE

| Compound | Change in Mean Blood Pressure |
|---|---|
| cis-1,2,3,4-tetrahydro-3-[(1-methylethyl)-amino]-2-naphthaleneol, hydrochloride | 2 |
| trans-1,2,3,4-tetrahydro-3-[(1-methylethyl)-amino]-2,6-naphthalenediol | 3 |
| trans-1,2,3,4-tetrahydro-3-[(1-methylethyl)-amino]-2,7-naphthalenediol | 3 |
| trans-7-[(1,1-dimethylethyl)amino]-5,6,7,8-tetrahydro-1,6-naphthalenediol | 1 |
| trans-6-[(1,1-dimethylethyl)amino]-5,6,7,8-tetrahydro-1,7-naphthalenediol | 1 |
| trans-1,2,3,4-tetrahydro-5-methoxy-3-[(1-methylethyl)amino]-2-naphthalenol | 3 |
| trans-1,2,3,4-tetrahydro-3-[(1-methylethyl)-amino]5,8-dimethoxy-2-naphthalenol | 2* |
| trans-6-dimethylamino-5,6,7,8-tetrahydro-1,7-naphthalenediol | 3 |
| trans-1,2,3,4-tetrahydro-3-[(1-methyl-ethyl)amino]-2-naphthalenol | 3 |
| 6,7-trans-5,6,7,8-tetrahydro-7-(iso-propylamino)-1,6-naphthalenediol, hydrochloride | 3 |
| 6,7-trans-5,6,7,8-tetrahydro-6-(iso-propylamino)-1,7-naphthalenediol, hydrochloride | 3 |
| trans-5,6,7,8-tetrahydro-7-[(1-methylethyl)-amino]-1,6-naphthalenediol | 1 |
| trans-5,6,7,8-tetrahydro-6-[(1-methylethyl)-amino]-1,7-naphthalenediol | 3 |
| trans-7-(dimethylamino)-5,6,7,8-tetrahydro-1,6-naphthalenediol | 3 |
| trans-5,6,7,8-tetrahydro-7-(methylamino)-1,6-naphthalenediol, acetate salt | 3 |

*Showed no effect in a separate run.

What is claimed is:

1. A method of lowering the blood pressure of a mammalian host in need thereof which comprises orally administering to said mammalian host an effective dose of a compound having the structure

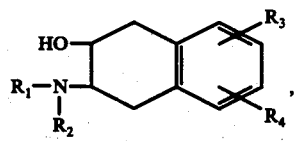

or a pharmaceutically acceptable salt thereof, wherein $R_1$ is hydrogen or alkyl; $R_2$ is alkyl; and $R_3$ and $R_4$ are each hydrogen, hydroxyl, alkoxy, or arylalkoxy, at least one of $R_3$ and $R_4$ being other than hydroxyl; wherein the terms alkyl and alkoxy refer to groups having 1 to 8 carbon atoms and wherein the term arylalkoxy refers to an alkoxy group substituted with phenyl or mono- or di-substituted phenyl wherein the substituents are halogen, alkyl or alkoxy.

2. A method in accordance with claim 1 wherein the compound has the structure

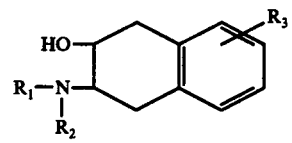

3. A method in accordance with claim 2 wherein the compound has the structure

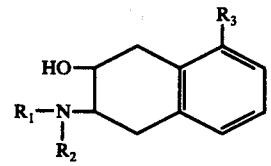

4. A method in accordance with claim 2 wherein the compound has the structure

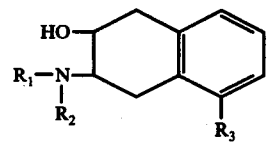

5. A method in accordance with claim 1 wherein $R_1$ is hydrogen and $R_2$ is alkyl.

6. A method in accordance with claim 1 wherein $R_3$ and $R_4$ are each alkoxy.

7. A method in accordance with claim 1 wherein the compound administered is 6,7-trans-5,6,7,8-tetrahydro-7-(isopropylamino)-1,6-naphthalenediol, hydrochloride.

8. A method in accordance with claim 1 wherein the compound administered is 6,7-trans-5,6,7,8-tetrahydro-6-(isopropylamino)-1,7-naphthalenediol, hydrochloride.

9. A method in accordance with claim 1 wherein the compound administered is trans-7-(dimethylamino)-5,6,7,8-tetrahydro-1,6-naphthalenediol.

10. A method in accordance with claim 1 wherein the compound administered is trans-6-(dimethylamino)-5,6,7,8-tetrahydro-1,7-naphthalenediol.

11. A method in accordance with claim 1 wherein the compound administered is trans-1,2,3,4-tetrahydro-3-[(1-methylethyl)amino]-5,8-dimethoxy-2-naphthalenol.

12. A method in accordance with claim 1 wherein the compound administered is trans-5,6,7,8-tetrahydro-7-[(1-methylethyl)amino]-1,6-naphthalenediol.

13. A method in accordance with claim 1 wherein the compound administered is trans-5,6,7,8-tetrahydro-6-[(1-methylethyl)amino]-1,7-naphthalenediol.

14. A method in accordance with claim 1 wherein the compound administered is trans-7-[(1,1-dimethylethyl)amino]-5,6,7,8-tetrahydro-1,6-naphthalenediol.

15. A method in accordance with claim 1 wherein the compound administered is trans-6-[(1,1-dimethylethyl)amino]-5,6,7,8-tetrahydro-1,7-naphthalenediol.

16. A method in accordance with claim 1 wherein the compound administered is trans-1,2,3,4-tetrahydro-5-methoxy-3-[(1-methylethyl)amino]-2-naphthalenol.

17. A method in accordance with claim 1 wherein the compound administered is trans-1,2,3,4-tetrahydro-3-[(1-methylethyl)amino]-2,6-naphthalenediol.

18. A method in accordance with claim 1 wherein the compound administered is trans-1,2,3,4-tetrahydro-3-[(1-methylethyl)amino]-2,7-naphthalenediol.

19. A method in accordance with claim 1 wherein the compound administered is cis-1,2,3,4-tetrahydro-3-[(1-methylethyl)amino]-2-naphthalenol, hydrochloride.

20. A method in accordance with claim 1 wherein the compound administered is trans-1,2,3,4-tetrahdyro-3-[(1-methylethyl)amino]-2-naphthalenol.

* * * * *